United States Patent
Notohara et al.

(10) Patent No.: US 11,278,252 B2
(45) Date of Patent: Mar. 22, 2022

(54) EXPOSURE-DOSE DISPLAY DEVICE

(71) Applicant: Shimadzu Corporation, Kyoto (JP)

(72) Inventors: Daisuke Notohara, Kyoto (JP); Shinsuke Kanazawa, Kyoto (JP); Tomoharu Okuno, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/629,241

(22) PCT Filed: Mar. 28, 2018

(86) PCT No.: PCT/JP2018/012913
§ 371 (c)(1),
(2) Date: Jan. 7, 2020

(87) PCT Pub. No.: WO2019/064652
PCT Pub. Date: Apr. 4, 2019

(65) Prior Publication Data
US 2020/0214657 A1     Jul. 9, 2020

(30) Foreign Application Priority Data
Sep. 27, 2017   (JP) .............................. JP2017-186486

(51) Int. Cl.
*A61B 6/00*   (2006.01)
*G01T 1/02*   (2006.01)

(52) U.S. Cl.
CPC ................ *A61B 6/463* (2013.01); *G01T 1/02* (2013.01)

(58) Field of Classification Search
CPC ........... A61B 6/463; G01T 1/02; G16H 30/20
See application file for complete search history.

(56) References Cited

U.S. PATENT DOCUMENTS

| | | | |
|---|---|---|---|
| 9,006,663 B2* | 4/2015 | Williams | ................ G01T 1/105 250/362 |
| 10,422,886 B1* | 9/2019 | Krishnareddy | ....... A61N 5/1071 |
| 2018/0368800 A1* | 12/2018 | Ishii | ........................ A61B 6/107 |

FOREIGN PATENT DOCUMENTS

| | | |
|---|---|---|
| JP | 2013113844 A | 6/2013 |
| JP | 2014-236798 A | 12/2014 |
| JP | 2015167695 A | 9/2015 |

OTHER PUBLICATIONS

Sailer et al., Real-Time Patient and Staff Radiation Dose Monitoring in IR Practice, Dec. 9, 2016, Cardiovasc Intervent Radiol vol. 40, pp. 421-429. (Year: 2016).*

(Continued)

*Primary Examiner* — Christine S. Kim
(74) *Attorney, Agent, or Firm* — Muir Patent Law, PLLC

(57) ABSTRACT

A workstation 5 links an X-ray image conforming to the Dicom standard and exposure dose data prepared by an exposure measurement system 7 with use of information on the imaging date and time of the X-ray image conforming to the Dicom standard and information on the imaging date and time of the exposure dose data prepared by the exposure measurement system 7. This enables the workstation 5 to calculate an exposure dose corresponding to each X-ray image. Also, the workstation 5 calculates an exposure dose corresponding to each X-ray examination on the basis of data on the start time and end time of the examination received from a console part 1. An examination time and an imaging technique at each examination, data including information on a subject, and information indicating an exposure dose corresponding to the examination are configured as one piece of data and displayed on a display part 51 of the workstation 5.

3 Claims, 4 Drawing Sheets

(56) References Cited

OTHER PUBLICATIONS

DoseAware Base StationPackage Instructions for Use. Manual [online]. Philips Corporation, 2010 [retrieved on Mar. 2, 2021], Retrieved from the internet from the FCC ID database: <https://fccid.io/XWK8603021/User-Manual/User-manual-Dose-aware-1228983.pdf>. (Year: 2010).*

Toyo Medic Co., Ltd. Web site (https://www.toyo-medic.co.jp/products/qcqa_rd/medical_staff_ec/raysafei2/). Website document submitted was downloaded on or about Nov. 25, 2019 (current understanding is that the submitted website document may be the same or substantially similar to information that was available on or about Sep. 14, 2017).

RaySafeTM Product Leaflet and Web site (http://www.raysafe.com/products/real-time-dosimetry-systems/raysafe-12/) Website document submitted was downloaded on or about Oct. 16, 2019 (current understanding is that the submitted website document may be the same or substantially similar to information that was available on or about Mar. 14, 2018).

Written Opinion of the International Search Authority (PCT/ISA/237) dated Jun. 19, 2018 for PCT application PCT/JP2018/012913, submitted with a machine translation.

First Japanese Office Action dated Aug. 4, 2020 for the corresponding Japanese Patent Application No. 2019-544224, with its machine translation.

* cited by examiner

FIG.4

| 1 | Month/Day/Year    Hour/Minute    General imaging <br> Name: ○○○○    45 years old   Male   Chest <br> Exposure dose: XXX Gy |
|---|---|
| 2 | |
| 3 | |

EXPOSURE-DOSE DISPLAY DEVICE

TECHNICAL FIELD

The present invention relates to an exposure dose display device for displaying an exposure dose of an operator such as an X-ray laboratory technician or a doctor.

BACKGROUND ART

When performing examination or treatment using an X-ray imaging apparatus, it is necessary to take account of not only exposure of a subject but also operator exposure of an operator whose performs such work on a daily basis, such as an X-ray laboratory technician or a doctor. For the operator exposure, it is effective to visualize exposure dose distribution on a dominant hand easily to be exposed, in the vicinity of both eyeballs easily to be damaged by X-rays, or in the vicinity of the thyroid gland.

As a system for displaying such an exposure dose, there has been proposed an exposure measurement system that records an exposure dose measured by a personal dosimeter together with time information. "RaySafe i2" as a real-time exposure measurement system by Toyo Medic Co., Ltd. is configured to include a touch-panel type screen installed in an examination room, and communicate with a personal dosimeter within a communicable range to display a real-time exposure dose. "RaySafe i2" is configured to display a current exposure dose level and an integrated dose value on the touch-panel type screen for each personal dosimeter worn by each operator (see Non-Patent Literatures 1 and 2).

In such an exposure measurement system, information on an exposure dose and information on exposure time at which corresponding exposure is received are generally adapted to be stored in a storage part once and be able to be outputted as tabular data corresponding to general-purpose software.

CITATION LIST

Patent Literatures

Non-Patent Literature 1: "RaySafe i2" (Real-time exposure measurement system), Toyo Medic Co., Ltd., searched for on Sep. 14, 2017 on the Internet <URL: http://www.toyo-medic.co.jp/seihin/catg03/raysafei2.html>

Non-Patent Literature 2: RaySafe i2 (Product Leaflet), Unfors RaySafe AB, searched for on Mar. 14, 2018 on the Internet <URL: http://www.raysafe.com/Products/Staff/RaySafe %20i2#Downloads>

SUMMARY OF INVENTION

Technical Problem

As described in Non-Patent Literature 1, there have been proposed some devices adapted to perform monitoring by displaying the integrated value and the like of an exposure dose measured by a personal dosimeter; however, it has not been possible to recognize which X-ray examination each exposure is made at. If it becomes possible to visualize information on which X-ray examination an exposure is made at, it is expected to be able to reduce an exposure dose by improving operations or the like at each examination.

The present invention has been made in order to solve the above-described problem, and intends to provide an exposure dose display device capable of displaying an exposure dose corresponding to each X-ray examination.

Solution to Problem

A first aspect of the present invention includes: an exposure dose data storage part that stores exposure dose data indicating the relationship between exposure dose information and exposure time information; an X-ray image storage part that, together with imaging time information given to an X-ray image, stores the X-ray image imaged by an X-ray imaging apparatus when performing an X-ray examination; an information linking part that links the exposure dose data stored in the exposure dose data storage part and the X-ray image stored in the X-ray image storage part with use of the exposure time information and the imaging time information; and an exposure dose display part that, on the basis of the exposure dose data and the X-ray image that are linked by the information linking part, displays the exposure dose corresponding to the X-ray examination or the exposure dose corresponding to the X-ray image at the X-ray examination.

A second aspect of the present invention is the first aspect of the present invention in which the exposure dose data indicating the relationship between the exposure dose information and the exposure time information is prepared by an exposure measurement system that records an exposure dose measured by a personal dosimeter together with time information.

Advantageous Effects of Invention

According to the first aspect of the present invention, an exposure dose corresponding to each X-ray examination or each X-ray image can be displayed by linking exposure dose data and an X-ray image with use of exposure time information and imaging time information. In doing so, it is possible to visualize information on which X-ray examination or X-ray image acquisition an exposure is made at, and therefore an exposure dose can be reduced by improving operations or the like at each examination.

According to the second aspect of the present invention, an exposure dose corresponding to each X-ray examination or each X-ray image can be easily displayed by directly using exposure dose data prepared by the exposure measurement system that records an exposure dose measured by a personal dosimeter together with time information.

BRIEF DESCRIPTION OF DRAWINGS

FIG. 4 is a schematic diagram illustrating data on an exposure dose corresponding to each X-ray examination prepared by a workstation 5.

DESCRIPTION OF EMBODIMENTS

Figure 1:
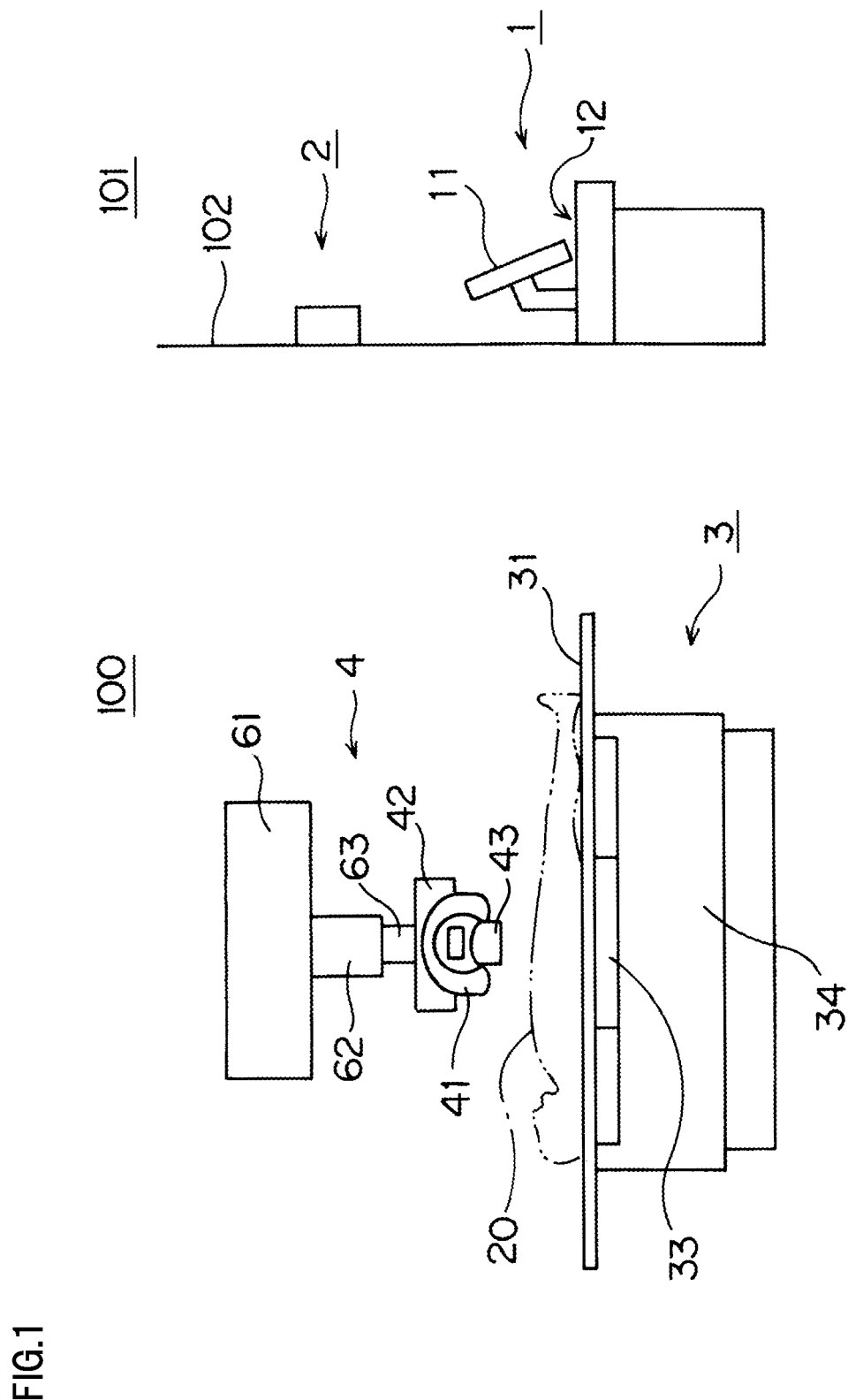
FIG. 1 is a schematic diagram of an X-ray imaging apparatus used for the exposure dose display device according to the present invention.

In the following, an embodiment of the present invention will be described on the basis of the drawings. FIG. 1 is a schematic diagram of an X-ray imaging apparatus used for the exposure dose display device according to the present invention.

The X-ray imaging apparatus includes: a console part 1 and a high voltage device 2 that are installed in an operation room 101 for an operator to perform X-ray imaging operations; and an examination table 3 and an imaging part 4 that are installed in an imaging room 100 for performing imaging on a subject 20. The imaging room 100 and the operation room 101 are blocked by a partition wall 102.

The console part 1 installed in the operation room 101 includes a display part 11 configured of a liquid crystal display and the like and an operation part 12 configured of a keyboard, a mouse, and the like for performing various types of operations, and is one for performing the various types of operations for performing X-ray imaging. In addition, the high voltage device 2 disposed on the partition wall 102 in the operation room 101 includes an operation panel having: a display part configured of a touch panel type liquid crystal display and the like; and various types of input buttons, and a push button switch for starting X-ray irradiation. The high voltage device 2 is one for setting the tube voltage and tube current of the below-described X-ray tube 42 or X-ray irradiation conditions such as an X-ray irradiation time.

The examination table 3 installed in the imaging room 100 includes: a top board 31 on which the subject 20 is placed; an X-ray detection part 33 containing inside a flat panel detector (FPD) as an X-ray detector; and a lifting/lowering part 34 for lifting/lowering the top board 31 and the X-ray detection part 33. The X-ray detection part 33 is adapted to be horizontally movable in the left-right direction in FIG. 1. Also, the X-ray detection part 33 is adapted to be liftable/lowerable in the up-down direction in FIG. 1 together with the top board 31. Further, the imaging part 4 installed in the imaging room 100 includes: a base part 61 that is movable in two directions mutually orthogonal with respect to the ceiling of the imaging room 100; a support part 62 extending downward from the base part 61; a movement part 63 that lifts/lowers and rotationally moves with respect to the support part 62; and a handle 41, the X-ray tube 42, and a collimator 43 integrally supported by the lower end part of the movement part 63.

X-rays radiated from the X-ray tube 42 onto the subject 20 via the collimator 43 are detected by the X-ray detection part 33. An X-ray image detected by the X-ray detection part 33 is transmitted to the below-described workstation 5 and server 6 via the console part 1. At this time, the start time and end time of the examination are transmitted together with the X-ray image.

Figure 2:
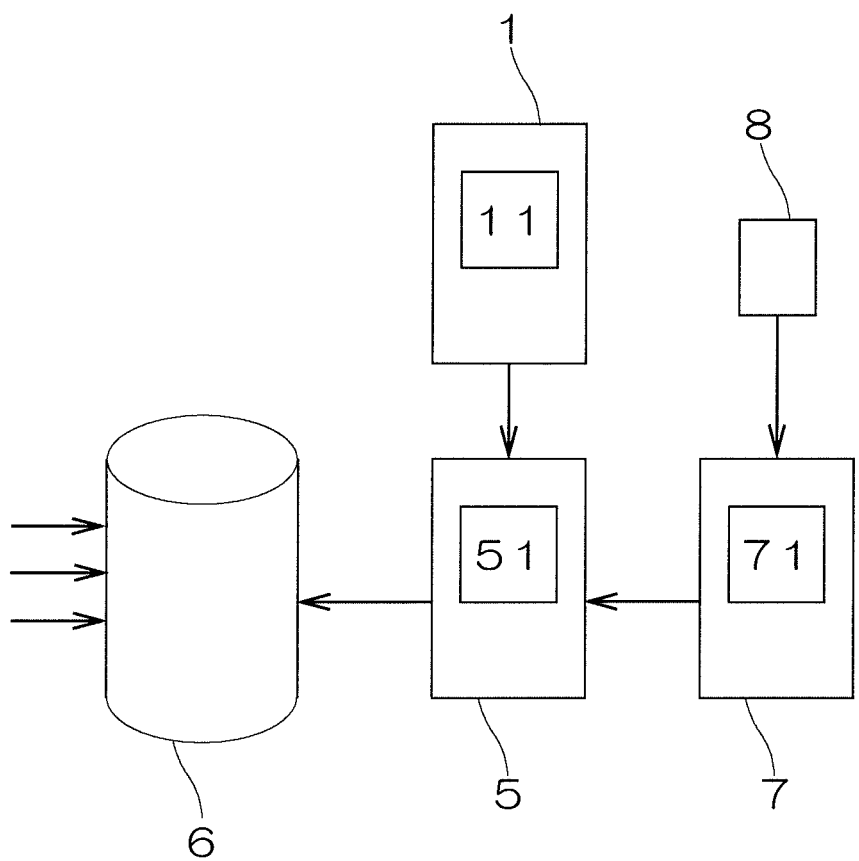
FIG. 2 is a block diagram illustrating the configuration of the exposure dose display device according to the present invention.

FIG. 2 is a block diagram illustrating the configuration of the exposure dose display device according to the present invention.

As described above, the console part 1 illustrated in FIG. 1 is connected to the workstation 5 and transmits an X-ray image to the workstation 5. The X-ray image is an image conforming to the Dicom standard. Note that Dicom stands for Digital Imaging and COmmunications in Medicine, and refers to a standard that defines the format of medical images imaged by CT, MRI, CR, and the like, which was developed by American College of Radiology (ACR) and National Electrical Manufacturers Association (NEMA), and a communication protocol between medical imaging equipment that handles such images.

The workstation 5 transmits the X-ray image and other pieces of data to the server 6. The server 6 is connected to multiple workstations 5 installed in a hospital, and used to store various types of images imaged in the hospital. Also, the workstation 5 is connected to the exposure measurement system 7 that records an exposure dose measured by a personal dosimeter 8 worn by an operator together with time information. For example, as disclosed in Non-Patent Literature 1, the exposure measurement system 7 includes a touch panel type screen and the like installed in the imaging room 100, and is configured to communicate with a personal dosimeter 8 within a communicable range to display a real-time exposure dose and also store the exposure dose. In addition, a personal dosimeter 8 is mounted by an operator constantly on his/her clothing or the like, and constantly measures an exposure dose at the time of daily examination or treatment.

Figure 3:
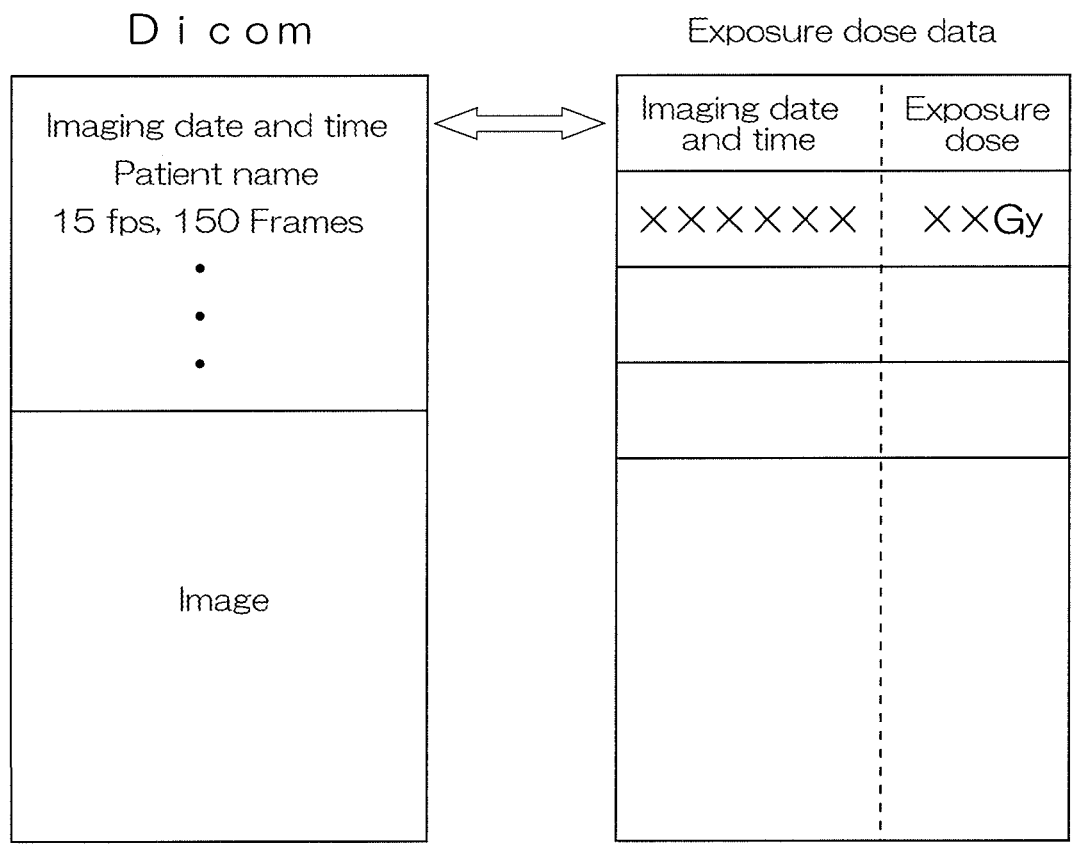
FIG. 3 is a schematic diagram illustrating the structure of an X-ray image that is prepared by a console part 1 in the X-ray imaging apparatus and conforms to the Dicom standard, and the structure of exposure dose data prepared by an exposure measurement system 7.

FIG. 3 is a schematic diagram illustrating the structure of an X-ray image that is prepared by the console part 1 in the X-ray imaging apparatus and conforms to the Dicom standard, and the structure of exposure dose data prepared by the exposure measurement system 7.

The X-ray image confirming to the Dicom standard consists of: an information area in which various types of information are recorded, such as an imaging date and time, a patient name, and imaging conditions; and an image area in which an image is recorded. On the other hand, the exposure dose data prepared by the exposure measurement system 7 is structured to link the imaging date and time and an exposure dose at the time. The workstation 5 illustrated in FIG. 3 links the X-ray image conforming to the Dicom standard and the exposure dose data prepared by the exposure measurement system 7 with use of the information on the imaging date and time in the X-ray image conforming to the Dicom standard and the information on the imaging date and time in the exposure dose data prepared by the exposure measurement system 7. In addition, the workstation 5 calculates an exposure dose corresponding to each X-ray image. Also, the workstation 5 calculates an exposure dose corresponding to each X-ray examination on the basis of data on the start time and end time of the examination received from the console part 1. The workstation 5 functions as an information linking part according to the present invention.

FIG. 4 is a schematic diagram illustrating data on an exposure dose corresponding to each X-ray examination prepared by the workstation 5.

As illustrated in this diagram, an examination time and an imaging technique at each examination, data including information on a subject 20, and information indicating an exposure dose corresponding to the examination are configured as one piece of data. This data is displayed on a display part 51 of the workstation 5. In addition, this data may be adapted to be displayed on the display part 11 of the console part 1 and/or on a display part 71 of the exposure measurement system 7 as well.

Further, this data may be adapted to be displayed by being printed out, instead of being displayed on the display part 51 of the workstation 5, the display part 11 of the console part 1, or the display part 71 of the exposure measurement system 7. The term "display" in this specification is a concept including such a form.

This enables operators and third persons to grasp an exposure dose of each operator corresponding to each X-ray examination. For this reason, it becomes possible to visualize information on which X-ray examination an exposure is made at and reduce an exposure dose by improving operations or the like at each examination.

In addition, as shown in FIG. 4, instead of displaying data on an exposure dose corresponding to each X-ray examination, it may be adapted to individually display data on an exposure dose corresponding to each X-ray image. In this case, it becomes possible to visualize information on what kind of X-ray imaging an exposure is made at.

REFERENCE SIGNS LIST

1: Console part
2: High voltage device
3: Examination table
4: Imaging part
5: Workstation
6: Server
7: Exposure measurement system
8: Personal dosimeter
11: Display part
12: Operation part
20: Subject
31: Top board
33: X-ray detection part
42: X-ray tube
43: Collimator
51: Display part
71: Display part
100: Imaging room
101: Operation room

We claim:

1. An exposure dose display device comprising:
an exposure dose data storage part that stores exposure dose data indicating a relationship between an exposure dose and an exposure time;
an X-ray image storage part that, together with imaging time given to an X-ray image, stores the X-ray image imaged by an X-ray imaging apparatus when performing an X-ray examination;
an information linking part that links the exposure dose data stored in the exposure dose data storage part and the X-ray image stored in the X-ray image storage part by using the exposure time and the imaging time; and
an exposure dose display part that, on a basis of the exposure dose data and the X-ray image that are linked by the information linking part, displays the exposure dose corresponding to the X-ray image at the X-ray examination.

2. The exposure dose display device according to claim 1, wherein
the exposure dose data is prepared by an exposure measurement system that records the exposure dose measured by a personal dosimeter together with the exposure time information.

3. The exposure dose display device according to claim 1, wherein the information linking part is configured by a workstation.

* * * * *